Figure 1:
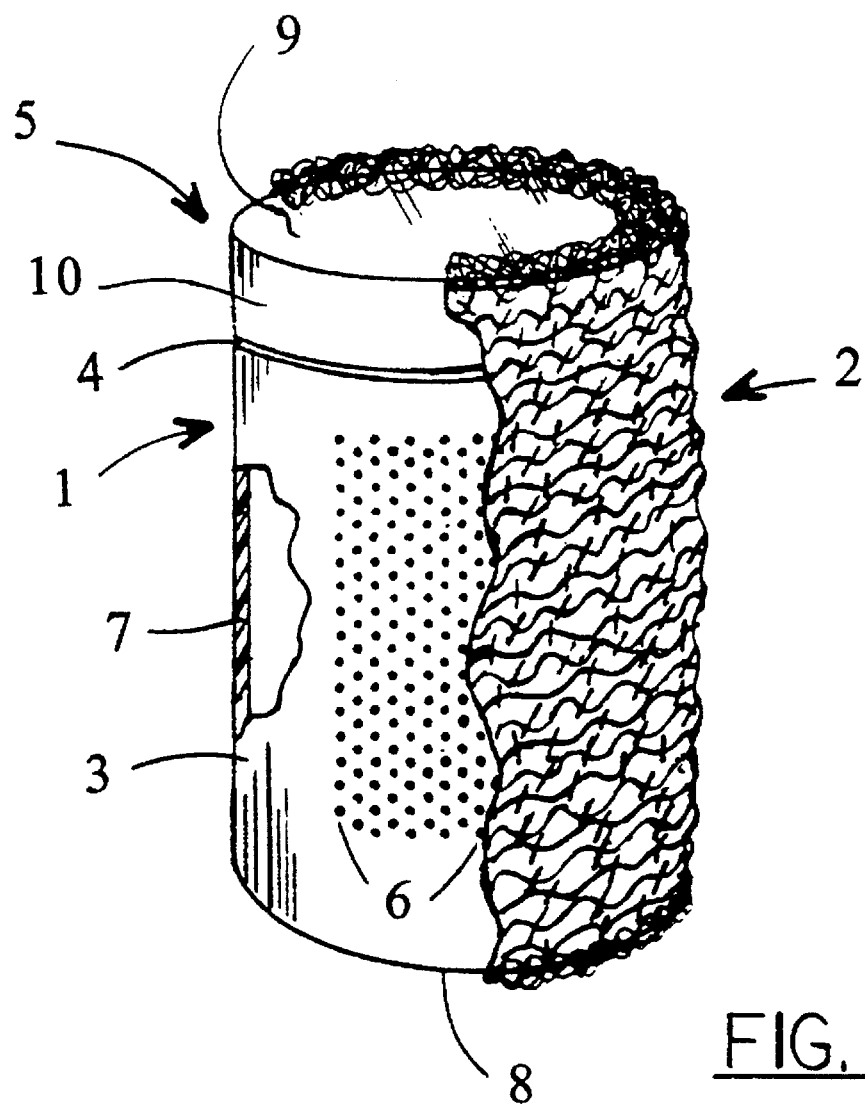

United States Patent

Mosley

[11] Patent Number: 5,584,871
[45] Date of Patent: Dec. 17, 1996

[54] EXPRESSIBLE COMPRESS

[76] Inventor: Keith A. Mosley, 439 Shannon Dr., Atlanta, Ga. 30310

[21] Appl. No.: 572,885

[22] Filed: Dec. 18, 1995

[51] Int. Cl.⁶ ........................................ A61F 7/00
[52] U.S. Cl. .................... 607/108; 607/109; 607/110
[58] Field of Search ............... 607/108–110, 111–114, 607/96, 104; 62/529, 259.3, 459, 460; 383/901

[56] References Cited

U.S. PATENT DOCUMENTS

| | | | |
|---|---|---|---|
| 1,744,423 | 1/1930 | Toadvine | 607/114 |
| 4,832,030 | 5/1989 | De Canto | 607/109 |
| 5,005,374 | 4/1991 | Spitler | 607/108 |

FOREIGN PATENT DOCUMENTS 292913  12/1918  Germany ............................. 607/114

Primary Examiner—Lee S. Cohen
Assistant Examiner—Herman J. Robinson

[57] ABSTRACT

An expressible compress is provided having a container with a perforatible wall through which fluids pass into an engulfing absorbent cloth sleeve to create a moist compress. The container has an open top body formed from a resilient plastic material and is adapted to be collapsed upon application of slight hand pressure and a cap for closing the top through which the container is filled.

2 Claims, 1 Drawing Sheet

EXPRESSIBLE COMPRESS

FIELD OF THE INVENTION

This invention relates to a expressible compress with the primary object of providing, in a manner hereinafter set forth, a novel means of administering moist cooling relief, to the skin's surface and body parts, from heat discomfort brought on by recreational and physical activity and/or high temperatures. It relates more specifically to a collapsible-permeable-wall container covered by an absorbent cloth sleeve with which a user can create a cool moist compress by alternative modes of operation of either cooperative collapsing of the container wall to forcibly expel water through its pores or seepage.

BACKGROUND OF THE INVENTION

Current means of heat-related relief from recreational activity and physical exertion are liquids from a sport bottle, toweling off, and the external use of ice. Toweling merely dries the surface of the skins but does not cool it. The primary goal of liquids from a sport bottle is to replenish body fluids and assist in lowering the internal body temperature, subsequently lowering the skin's surface temperature if the person is not in direct sunlight such as that experienced on a tennis court. Athletes and workers on occasions will place the outer surface of a chilled container against their skin for quick external relief. Ice applied directly to the skin can only be tolerated for brief periods and the use of a cloth is usually employed to facilitate holding the ice and to absorb melting. The resulting damp cloth is converted to a cold compress. The means heretofore available are not direct convenient modes of lowering the skin's temperature and providing cool-relief.

Occupants of vehicles lacking functioning air-conditioners carry cloth hand-towels and face-cloth to wipe away perspiration. Cloths moistened with water before venturing into the heat are usually dry before the return trip has ended. A hand-towel would have to be dripping wet in order to remain moist after an hour or so of heat exposure and the user would not be receptive to wetting his clothing or upholstering.

A cold compress applied to the back of the neck is a common practice for slowing or stopping a nose bleed. The heat exchanged between the compress and the skin results in the compress needing to be replenished with either cold water or ice.

The present invention comprises a resealable container, with perforatible indentations on its surface which allows the regulation of the amount of fluid released, and an absorbent cloth sleeve covering. Ice and/or fluid is placed into the resealable container and the sealed container is placed inside the cloth sleeve. Squeezing or osmosis will cause water to flow through the perforations and into the cloth, thus creating and maintaining a cool damp compress to be applied to the skin.

Another very important object of the present invention is to provide a absorbent surface to remove perspiration from the skin.

Another very important object of the present invention is to provide a cylindrical shaped massaging unit which can be rolled or knead atop various body parts.

Another very important object of the present invention is to provide a cold compress for medicinal use to combat nose bleeds.

SUMMARY OF THE INVENTION

In accordance with this invention, a cloth covered container with a perforatible surface is provided for athletes, recreationors, heat-sufferers and workers which can be utilized in accordance with either technique of releasing fluid, i.e., either by expression or by seepage of the fluid into the cloth covering through perforated holes. The container embodies a conventional structure and is fabricated from a plastic material such as by blow molding process. This container has a wall structure of a thickness such that it may be collapsed with moderate hand pressure. A open top is provided with a cap that is removable for purposes of inserting ice and/or fluids. In accordance with this invention, portions of the wall's surface has perforatible indentations that regulate the flow of fluid, i.e., the amount of fluid released increases with each additional hole punched.

In accordance with this invention, the cloth sleeve is of a design to permit a snug fit between the assembled container and the cloth to prevent the container from slipping out and facilitate the absorption process.

These together with other objects and advantages which will become subsequently apparent reside in the details of construction and operation as more fully hereinafter described and claimed, reference being had to the accompanying drawings forming a part hereof, wherein like numerals refer to like parts throughout, and in which:

FIG. 1 is an elevational view of a container and cloth sleeve assembly embodying this invention.

Referring now to the drawing in detail, it will be seen that the embodiment of the invention which has been illustrated comprises a container 1 and a cloth sleeve 2 in assembled relationship. This container 1 is of a conventional shape and includes a body portion 3 of elongated cylindrical configuration having a opening at the top defined by a neck structure 4. This neck portion is not shown in greater detail, but does include a screw thread which is designed to interengage with an internal thread formed on the interior of a cap 5 adapted to be removably applied to the container. While the illustrative embodiment of the cap and container is shown and illustrated as having a screw thread type of interconection, it will be understood that other means of interconnecting caps and containers may be employed.

The container 1 as indicated is formed by a blow molding process from an appropriate type of plastic material. The material that is used is of a type having resilience such that when the wall structure is collapsed and the pressure is removed, the wall structure will return to its original shape. Such a container structure also has a relatively thin wall 7 throughout a substantial part of the body portion 3. Indentations 8 on the outer surface of the wall structure are created during the molding process. Other means of designating surface area for piercing and/or pre-cut holes may be used. A typical container 1 has dimensions of the order of 2" diameter with a length of the order of 4", such that it can fit comfortably in an adult's hand, but can be molded in smaller or larger dimensions.

The cap 5 comprises a flat top wall 9 that is interconnected with a flange 10 that is adapted to fit over and mechanically interengage with neck structure 4. Turning the cap onto the neck structure will cause the cap's internal thread and the neck's screw thread to pull the cap down tightly onto the neck structure and form a sealed engagement to prevent fluid flow as between the cap rand the neck. The flange 10 will align with wall structure 7, creating a continuous surface, when the cap is engaged.

The cloth sleeve 2 is comprised of an absorbent material, woven into a cylindrical shaft, with elastic characteristics that permit the sleeve to be fixed very firmly in place. The open-ended sleeve will extend beyound the top and bottom of the assembled container enough to engulf the rims, therein providing cushioned edges. Other types and styles of coverings may be utilized for this purpose.

It is thought that the operation of the illustrative embodiments will be readily apparent from a consideration of the foregoing. Briefly, ice and/or water is placed into the container 1 and it is sealed with a cap 5. One or more indentations 8 are pierced to adjust the amount of water released before placing the sealed container 1 inside the cloth sleeve 2. Applying pressure to the container is one option for releasing the water into the cloth, therein creating a cool moist absorbent surface, and osmosis is another.

The foregoing is considered as illustrative only of the principles of the invention. Further, since numerous modifications and changes will readily occur to those skilled in the art, it is not desired to limit the invention to the exact construction, geometric shape and operation shown and described, and accordingly all suitable modification and equivalents may be resorted to, falling within the scope of the invention as claimed.

What is claimed as new is as follows:

1. A container and cloth sleeve assembly for use as an expressible compress comprising
   (A) a closed container for holding melting ice and/or fluid that may be selectively released into an outer cloth sleeve, said container has means to enable filling with ice and/or fluid, said container including a body portion having a wall structure of original shape formed with a predetermined thickness from a plastic material, thereby enabling at least portions of said wall structure having the characteristics of resilience whereby it will return to its original shape upon easing of collapsing force, said container having perforatible indentations formed in the wall structure for passage of fluid to its external surface;
   (B) a cloth sleeve, having open ends for insertion of said container, capable of absorbing expressed fluid and condensation, said sleeve woven into a cylindrical shaft, consisting of soft absorbent material with characteristics of elasticity whereby it will be fixed very firmly in place, which extends beyond the top and bottom of said container therein overlapping its rims.

2. A container and cloth sleeve assembly according to claim 1 wherein said means to enable filling, includes a cap, said body portion having an opening formed therein through which said container may be filled and emptied of ice and/or fluid and said cap is removably positionable on said body portion in closing relationship to said opening, said cap and body portion including mechanical means for cooperative interengagement in detachably securing of said cap in closing relationship to said opening and for effecting a fluid-sealed relationship therebetween when said cap is disposed in closing relationship to said opening.

* * * * *